United States Patent
Oyarzábal

(10) Patent No.: US 12,270,014 B2
(45) Date of Patent: Apr. 8, 2025

(54) METHOD OF PRODUCTION OF ALCOHOLIC BEVERAGES FROM CORN USING AN ALKALINE COOKING PROCESS, TREATMENT-USE OF ALKALINE COOKING RESIDUES FOR PRODUCTION OF DISTILLED ALCOHOL FOR PURPOSES OF HUMAN CONSUMPTION AND/OR INDUSTRIAL USE

(71) Applicant: CASA LUMBRE S.A.P.I DE C.V., Mexico City (MX)

(72) Inventor: Ivan Saldaña Oyarzábal, Mexico City (MX)

(73) Assignee: CASA LUMBRE S.A.P.I DE C.V., Mexico City (MX)

( * ) Notice: Subject to any disclaimer, the term of this patent is extended or adjusted under 35 U.S.C. 154(b) by 4 days.

(21) Appl. No.: 17/865,625

(22) Filed: Jul. 15, 2022

(65) Prior Publication Data
US 2023/0052560 A1 Feb. 16, 2023

(30) Foreign Application Priority Data
Jul. 16, 2021 (MX) .................. MXa2021008620

(51) Int. Cl.
*C12G 3/021* (2019.01)
*A23L 7/10* (2016.01)
(Continued)

(52) U.S. Cl.
CPC ............... *C12G 3/021* (2019.02); *A23L 7/107* (2016.08); *A23L 7/1975* (2016.08); *C12H 6/02* (2019.02); *A23V 2002/00* (2013.01)

(58) Field of Classification Search
CPC ............ C12G 3/021; A23L 7/107; C12H 6/02
(Continued)

(56) References Cited

U.S. PATENT DOCUMENTS

| 2,662,842 A | * | 12/1953 | Christensen | C12P 7/06 435/99 |
| 6,428,828 B1 | | 8/2002 | Jackson | |
| 2015/0368138 A1 | * | 12/2015 | Asaff Torres | C07C 51/487 210/632 |

FOREIGN PATENT DOCUMENTS

| MX | YU200300005 | 5/2005 |
| MX | 2017013218 | 4/2019 |
| MX | 2017016584 | 6/2019 |

OTHER PUBLICATIONS

Rojas, Lime Cooking Process: Nixtamilization Form Mexico To The World, Basic Concepts, 2016 accessed at https://repository.cimmyt.org/bitstream/handle/10883/18872/58123.pdf?sequence=1&isAllowed=y.*

(Continued)

*Primary Examiner* — Donald R Spamer
*Assistant Examiner* — Philip A Dubois
(74) *Attorney, Agent, or Firm* — Wissing Miller LLP

(57) ABSTRACT

A method for producing alcoholic beverages from alkaline cooking, using as a basis the increase in pH in the medium to cook cacahuazintle corn grains, other similar mealy corn or any other grain, which offers a different proposal due to the generation of flavors, aromas and sensory characteristics that differentiate the products obtained by the methods herein disclosed from existing alcoholic beverages. A method for producing alcohol for human consumption and/or industrial use from the recovery and treatment of nejayote obtained from alkaline cooking residues, also known as nixtamalization of corn, applied to any alkaline cooking residue in the alimentary field.

3 Claims, 4 Drawing Sheets

(51) Int. Cl.
*A23L 7/104* (2016.01)
*C12H 6/02* (2019.01)

(58) Field of Classification Search
USPC .......................................................... 426/11
See application file for complete search history.

(56) References Cited

OTHER PUBLICATIONS

Dutton, How Corn is Processed to Make Ethanol, PSU, 2014, accesed at https://www.e-education.psu.edu/egee439/node/673 (Dutton).*

Arora, Effects of high temperature drying air on corn quality, Iowa State, 2003, accessed at https://dr.lib.iastate.edu/server/api/core/bitstreams/ac5d1113-e760-47fb-bfdd-e51bc552c857/content (Arora).*

Castillo V.K.C. et al., "Effect of calcium hydroxide concentration and cooking time of corn grain (*Zea mays* L.) nixtamalized, over physicochemical and rheological nixtamal characteristics.", Archivos Latinoamericanos de Nutrición 59(4), (2009) 425-432,10 pages.

Abstract of Gutiérrez-Uribe et al., "Phytochemical analysis of wastewater (nejayote) obtained after lime-cooking of different types of maize kernels processed into masa for tortillas", (2010) 7 pages.

Binder, Shawn, "Abasolo El Whisky De Mexico Stays Rooted In History", https://thedieline.com/blog/2020/8/5/abasolo-el-whisky-de-mexico, (2020) 6 pages.

Exended European Search Report mailed in corresponding EP 22185296.5 on (Feb. 28, 2023) 12 pages.

Abstract of Trejo, "The Role of Lime in the Alkaline Treatment of Corn for Tortilla Preparation", https://pubs.acs.org/doi/pdf/10.1021/ba-1982-0198.ch009, (1982).

Ramirez-Romero, "Study of Nejayote as Culture Medium For Probiotics and Producation of Bacteriocins", Revista Mexicana de Ingeniería Química, vol. 12, No. 3 (2013) 463-471.

* cited by examiner

METHOD OF PRODUCTION OF ALCOHOLIC BEVERAGES FROM CORN USING AN ALKALINE COOKING PROCESS, TREATMENT-USE OF ALKALINE COOKING RESIDUES FOR PRODUCTION OF DISTILLED ALCOHOL FOR PURPOSES OF HUMAN CONSUMPTION AND/OR INDUSTRIAL USE

CROSS-REFERENCE TO RELATED APPLICATIONS

This application claims priority benefits under 35 U.S.C. § 119 from Mexican Patent Application No. MX/a/2021/008620 filed on Jul. 16, 2021, which is incorporated herein in its entirety by reference.

FIELD OF THE INVENTION

The invention refers to an innovative method for producing fermented and distilled alcoholic beverages based on grains such as corn through an alkaline cooking process prior to the hydrolysis, fermentation and distillation processes.

It has been observed that, during the "nixtamalization" process, important physical-chemical changes occur that positively affect the sensory profile of the material subjected to the process, especially corn, where the intensity of the changes depends on the conditions of process, such as: 1. Cooking time, 2. Cooking temperature, 3. Pressure, 4. Rest time and 5. Alkalizing compound, that, although by definition and tradition the most used are lime or hearth ash, other compounds are not restricted, and 6. Raw material used (cacahuazintle corn, other mealy corn similar to some other grains).

Particularly, a different and innovative method is described in the production of spirits with respect to the existing ones. The method corresponds to the generation of flavors, aromas and special sensory characteristics provided by the alkaline treatment to which the grains are subjected, especially cacahuazintle maize and other similar floury maize, although the possibility of using other grains is not excluded.

Additionally, a method of treatment-use of alkaline cooking residues (called NEJAYOTE, in case of nixtamalization of corn) rich in organic material is described.

BACKGROUND OF THE INVENTION

Nixtamalization is a process historically used in the processing of corn for producing foods such as tortillas, dough and tamales to name a few; which consists of cooking the corn grain in an alkaline solution, commonly calcium hydroxide. (Castillo V. K. C., et al, 2009, Archivos Latinoamericanos de Nutrición, 59(4), 425-432). Nixtamalization processes generally begin with soaking the corn (or other grain) in hot water at a temperature slightly below 100° C. for a period of time between 15 and 60 minutes, with a 1:3 ratio (corn:water) and adding calcium hydroxide to prepare an alkaline solution, leaving the mixture to rest for 12 to 19 hours in the alkaline solution, then washing with enough clean water to remove the remains of the alkaline cooking, obtaining as a result a soft grain with a differentiated flavor, shelled (nixtamalized or nixtamal corn) and an aqueous solution known as nejayote (Trejo et al, 1982). However, the operating conditions may vary depending on the equipment available for said process.

Nejayote is the name given to the effluent from the nixtamalization or alkaline cooking process of corn, made up of waste from the water corresponding to the alkaline cooking and water from washing the corn grains. The nejayote has physical and chemical features that give it characteristics that have a negative impact on nature, such as: a high pH (pH=12), high chemical-biological oxygen demand and high concentrations of dissolved organic matter in the pericarp, endosperm, hemicellulose, carbohydrates, cellulose, protein, as well as carotenoids responsible for the yellow coloration (Gutiérrez-Uribe et al., 2010, Ramirez-Romero et al., 2013). Its treatment is important since currently not all nixtamalization residues are disposed of correctly, but rather they are disposed of directly in the drainage generating a negative impact on the environment. For example, the high chemical demand for oxygen that these residues present, as well as the high content of organic and inorganic matter that must be oxidized, generate high concentrations of $CO_2$, which have repercussions on the generation of greenhouse gases. On the other hand, since it is disposed of directly into the drain, the water is contaminated with organic material, making it more difficult to treat.

There is no evidence or record of the use of nixtamalization of corn as a treatment prior to alcoholic fermentation, distillation and production of spirits; however, research has been carried out regarding nejayote for its treatment and reduction in environmental impact.

For example, Mexican patent No. MX/a/2017/016584, "Process for producing bioethanol, cell biomass and other metabolites from the insoluble fraction of nejayote", describes the obtaining of cell biomass, bioethanol and other metabolites from the insoluble fraction of nejayote either independently or with the union of other fractions of nejayote obtained by filtration, to obtain bioethanol, contemplating the processes of acidification of the medium, hydrolysis and sequential or simultaneous fermentation. This invention describes the process of using nejayote, starting with the acidification of the medium to a pH of 7 and heating at 70° C./15 min to carry out the hydrolysis of starches, later both the temperature and the pH of the solution are lowered and enzyme complexes are added to complete the hydrolysis. Finally the *K. marxianus* yeast is inoculated, being possible to carry out the inoculum after hydrolysis or simultaneously. As a fermentation product, ethanol is obtained in a concentration of 2 to 8% alcohol by volume, in addition to 1.75 to 3.5 mg/mL of biomass and approximately 4 g/L of other metabolites that depend on the fraction of nejayote used. However, this patent does not describe or suggest the use of ethanol for human consumption or for industrial use.

Mexican patent No. MX/a/2017/013218, "Process for obtaining hard fiber and nopal cuticle", discloses a process for obtaining two nopal products that involves separating the pulp from adult nopal leaves to its subsequent alkaline anaerobic fermentation, which occurs by submerging the plant material in nejayote for 7 to 8 days in containers with lids. The hard fiber product of the nopal is used as insoluble dietary fiber (additive in the food industry or nutritional supplement), whenever it is sterilized, composite in reinforcement materials of different construction areas, spare parts in diapers, matrices in digesters, materials for removal of contaminants, for example in wastewater, or industrial filters, among others, in a general way.

On the other hand, Mexican patent No. YU/E/2003/000055, "Process for using the effluent from corn nixtamalization (nejayote) to obtain microbial amylases", describes a process for preparing microbial amylases in submerged cultures using as main raw material, the effluents generated by the corn nixtamalization process, which are fermented by a selected strain of the filamentous fungus *Aspergilius awamori* 2B361. The aforementioned process consists of generating a monoculture of the aforementioned organism in a discontinuous process in a stirred tank where the nutrient medium is the effluents from the nixtamalization (nejayote), which contain a concentration of solids from the nixtamalized corn of 5 to 50% (w/v), and $Ca^{2+}$ (from the calcium hydroxide used during the nixtamalization of the corn) from 1 to 10% (w/v) and acid pH. After fermentation, an enzymatic preparation is obtained which is partially purified by means of a gradual precipitation with ammonium sulfate and finally crystallized after a lyophilization operation. However, this patent does not claim the production of ethanol from any procedure since it is focused solely on the preparation of amylases.

BRIEF DESCRIPTION OF THE INVENTION

The present invention is directly related to the production of spirituous beverages from an alkaline cooking of cacahuazintle corn or other similar mealy corn, without excluding the possible use of various species and other grains, the treatment-use of alkaline cooking residues for producing distilled alcohol for human consumption and/or industrial use.

The invention contemplates the following points:

1. Alkaline cooking of cacahuazintle maize (corn), namely "nixtamalization" (does not exclude the "nixtamalization" of other grains or other similar floury maize species), as a process that provides a differentiated and more intense sensory structure to the maize or the grain employed, through the use of calcium hydroxide, $(Ca(OH)_2)$ or another compound that raises the pH of the medium, under the understanding that nixtamalization is carried out in a solution with a high pH (pH=12±0.5).

2. Dehydration-Roasting of corn after alkaline cooking and prior to grain grinding, as an additional thermal process that removes moisture and can modify the organoleptic characteristics of the grain depending on the intensity of the process, allowing the processed grain not be subject to immediate processing.

3. Treatment-use of nejayote or alkaline cooking residues for producing alcohol suitable for human consumption or, failing that, for industrial use. This process begins by recovering the effluents from the alkaline cooking, subsequently adding corn flour (previously nixtamalized and dried-roasted corn; the method used to obtain the flour is not limiting for the present invention), hydrolytic enzymes, and preparing a must for fermentation and distillation.

After points 1 and 2, described above, the grinding processes, must preparation, hydrolysis of sugars and starches by means of hydrolytic enzymes and malt, alcoholic fermentation, distillation and aging in barrels (aging in barrels is optional and not limiting for the invention) are followed. The final product of this process is a differentiated alcoholic beverage, with a predominant flavor and aroma of corn.

Unlike traditional products produced from the fermentation of corn grains that do not undergo alkaline cooking (nixtamalization) in their process, the present invention seeks to differentiate the sensory profile of spirits prepared from corn grains (or other grains), enhancing its flavor.

Within the scope of the present invention, it is sought to solve the following disadvantages:

Spirit drinks with high oxidative potential and prone to developing sensory characteristics.

Products with high bitterness or lack of intensity and sensory complexity.

Products that need to spend time in barrels or be subjected to subsequent conditioning processes to be suitable for consumption, such as avocado.

On the other hand, unlike nejayote wastewater treatment processes, within the scope of the present invention, the use-treatment of nejayote wastewater is sought to generate a product for use and/or consumption from waste. With this, it is proposed to reduce the environmental impact represented by the remains of the nixtamal industry or any food industry that involves cooking grains in an alkaline solution.

BRIEF DESCRIPTION OF THE FIGURES

In order to give a better understanding of the invention, a description thereof is provided below, together with the accompanying figures, with a non-limiting illustrative nature.

DETAILED DESCRIPTION OF THE INVENTION

The production of whiskey is a well-known technique that has been adapted over the centuries, which has been modified by using different fermentable raw materials, for example, barley, wheat, rye and corn. After fermentation, the must is distilled and aged in different types of wooden barrels to generate a sensory difference.

Figure 1:
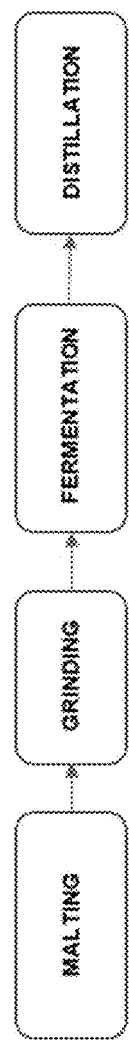
FIG. 1 shows a flow chart for whiskey production in the traditional way.

According to FIG. 1, the whiskey production process traditionally includes the Malting, Grinding, Fermentation and Distillation stages; which are detailed below.

Malting: Malting is an interrupted process of grain germination, which is called "malt". The process begins with the soaking of the grains for their enzymatic activation, later they are placed in a "rest" process through which germination begins in a period of 3 to 5 days, finally the grains are dried to stop the enzymatic activity.

Grinding: It is the process by which the grains are transformed into a fine flour, which is used for producing the must when mixed with water.

Fermentation: Fermentation corresponds to the addition of yeasts that transform the assimilable sugars contained in the must into alcohol.

Distillation: Distillation is a process where a mixture of water, alcohol and other aromatic compounds is subjected to a heat source to separate it into its components (water, alcohol and other compounds such as esters, organic acids and volatile compounds that confer characteristic flavors). The first distillation corresponds to the distillation of the dead must, in which alcohol, water, organic acids, aromatic compounds, among others, are separated from a mixture with organic solids; while in the second distillation (rectification), the alcohol, water, organic acids, esters, among others, are separated, which confer the characteristic flavor of the distilled alcoholic beverage.

Figure 2:
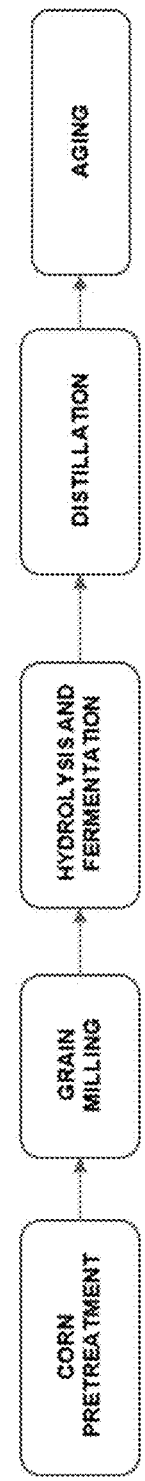
FIG. 2 shows a flow diagram of the method used for producing an alcoholic beverage according to the present invention, leaving aside the dehydration-roasting process, which does not limit this invention.
Figure 3:
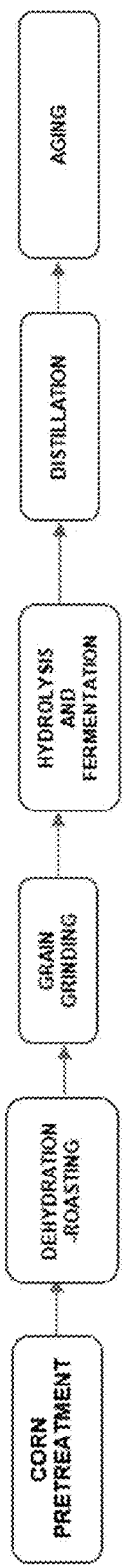
FIG. 3 shows the flow diagram corresponding to the method for producing alcoholic beverages according to the present invention in an embodiment that takes into account the dehydration-roasting process of the corn grains, which, although it is not limiting, substantially improves the final product.

According to the scope of the present invention, and taking FIGS. 2 and 3 into consideration, the method of the claimed invention comprises the stages of Alkaline corn cooking, Dehydration-Roasting, Grinding, Hydrolysis, Fermentation, Distillation, Rectification and Aging; these stages are detailed below:

Alkaline corn cooking (nixtamalization): The cacahuazintle corn or other mealy corn is received and evaluated taking into account different internal quality parameters such as aroma, impurities (% of defective corn kernels) and kernel moisture. Subsequently, it is placed in a cooking vat in which water and a compound that increases the pH in a range of 11 to 12.5 (KOH, NaOH, to mention a few, with $Ca(OH)_2$ being the preferred embodiment) are added, then cooked for a period of about 30 minutes, and left to rest for around 12 to 18 h. At the end of the rest time, it is rinsed with clean water until any trace of the alkaline solution is removed (2 to 3 hours of washing); the washing water and the effluent from the alkaline cooking are recovered for subsequent treatment-use, which is claimed in this document; finally, the corn is drained for a period of approximately 2 to 3 hours.

Dehydration-Roasting: As mentioned above, the dehydration-roasting process is the preferred embodiment for the present invention, which is not limiting thereof. Before starting the roasting of the grains, the corn must be pre-dried with hot air for 15 to 60 minutes at a temperature below 100° C. (preferably between 85 to 90° C.), then a visual and sensory control process is carried out to start with the increase in temperature; if the roasting-dehydration is within the established sensory and visual parameters, the process continues and the temperature is raised above 100° C. (preferably 100 to 115° C.) until it meets the specifications mentioned below:

The method must meet the following parameters:

| OPERATION | SENSORY | PARAMETERS |
|---|---|---|
| ALKALINE COOKING (NIXTAMALIZATION) | Whole grains light yellow in color, slightly moist, not sticky and with easily unfolding pericarp. Free from defects or unpleasant odors such as fermentation, rancidity, mold or any other foreign odor. | Accept or reject based on sensory specification |
| DEHYDRATION-ROASTING | It must be free of strange odors with a crunchy consistency, it must not feel chewy or floury in the central part, with light notes of roasted corn without reaching burnt notes. | Approved Corn Humidity: Medium: 4.0% + 0.3 (Slight notes of toasted corn without reaching burnt notes) Rejected Corn Humidity: 2.4 + 0.8 (Notes of Burnt Corn/Slight Notes of Smoke) Reprocessing Corn: Humidity: >4.5% (Moisture Notes/Slight Mass Notes/Stale Notes) |
| CORN MALTING | If the non-compliance is due to quality (% germination not reached), the germination can be accepted. If the non-compliance is due to safety (presence of fungus), the sprout must be rejected. | Soaking Stage: % humidity: 40% Germination Stage: Plumule Growth: 90% % Germinate. 90% |

Grinding: At the end of the roasting process, the grains are ground. This process is carried out to obtain a fine flour, which is added to a tank with water at 50° C. and dispersed in the liquid.

Hydrolysis: Once the fine flour is obtained in the grinding process, it is added to a tank with water at 50° C. for its dispersion in the liquid. Once the flour has been dispersed homogeneously, the pH is adjusted to 6 with hydrochloric acid (preferred for this embodiment, but not limited), for the optimal functioning of the hydrolytic enzymes (hydrolysis is carried out by adding hydrolytic enzymes and malted corn). Within the scope of the present invention, the hydrolytic enzymes can be heat-resistant alpha-amylases and amyloglucosidases.

Fermentation: Fermentation is done by adding yeasts capable of resisting high alcohol concentrations. Fermentation takes approximately 72 to 96 hours.

Distillation: The first distillation is carried out once the fermentation process is finished in a copper still (preferred but not limited), where the dead must is poured. The distillate is constantly sensorily evaluated until the liquid is separated into high and low ordinaries. They will be subjected to a rectification process (second distillation).

Aging in barrels: The product from the second distillation is evaluated sensorially and if approved, it is placed in barrels for aging (preferred, but not limited).

Figure 4:
FIG. 4 shows a flow diagram that includes the points contemplated by the present invention, which correspond to the alkaline cooking, the roasting process of the corn grains and the treatment-use of the alkaline cooking residues (nejayote) and the use of distillation residues.

FIG. 4 shows only the points included within the present invention, which include the following: alkaline cooking, dehydration-roasting of corn (mentioned above), as well as the treatment-use of wastewater (nejayote); the treatment-use process is described below for greater clarity.

Wastewater treatment (nejayote):
1. Recovering the residues from alkaline cooking (nixtamalization)
2. Acidifying the nejayote
3. Adding nixtamalized corn flour to the nejayote 4. Hydrolyzing the transformed nejayote (must)
5. Fermenting the must
6. Distilling the must.

In accordance with the present application, the corn is subjected to a process of cooking and soaking in an alkaline solution (nixtamalization) that modifies its physical and chemical characteristics, washing and removing compounds that have been solubilized before being hydrolyzed into fermentable sugars by means of addition of enzymes and malts that generate the breaking of alpha-D-1,4 glycosidic bonds, to later be subjected to an alcoholic fermentation process.

The physical and chemical changes that occur in the process modify and favorably affect the sensory and organoleptic characteristics of the spirits obtained from corn, delivering different, cleaner and more expressive distilled products. Firstly, the removal of pectins, hemicelluloses and insoluble fibers allows the hydrolysis processes based on malt or other enzymes to occur efficiently, as well as facilitating the gelatinization and dispersion processes at that stage. Calcium and phosphorus serve as nutrients for the yeasts during fermentation. The decrease in fat reduces the formation of bitter compounds or rancid notes in the resulting spirits. The development of aromatic compounds generated by associations in the raw material during alkaline cooking and, subsequently, derived from the different characteristics of the treated grains, in fermentation, result in sweeter, lighter products with a better sensory profile.

As has been mentioned before, within the scope of the application, any compound that increases the pH can be used as a base for cooking the grain, based on the understanding that since it is an alkaline treatment, any basic compound can help carry out a favorable alkaline cooking, taking into account that there are changes in cooking time, cooking temperature, pressure and other factors, depending on the nature of the corn or grain and the alkalizing compound.

In this sense, the invention to claim can be used for producing spirits that come from the fermentation of corn (or other grain), improving the sensory characteristics, and helping the processing thereof used as raw material. Within the scope of the claimed invention, without limiting the scope, "alcoholic beverage" means any spirituous beverage, but preferably "whiskey" in any of its varieties.

As a second embodiment of the claimed invention, the present application additionally describes a method for producing alcohol for human consumption and/or industrial use from the recovery and treatment-use of nejayote (alkaline cooking effluent with basic pH, high chemical and biological oxygen demand, in addition to other residual components of the raw material used), as it is one of the residues with the greatest impact on the environment. Given this information, its use in the production of alcohol for human consumption or for industrial use is of great importance in this research.

It is worth mentioning and emphasizing that, within the scope of this invention, said procedure for the treatment-use of nixtamalization residues is applicable to any area of the food industry in which an alkaline cooking process (nixtamalization) is carried out, and it can also be applied to the treatment-use of an alkaline cooking with compounds other than $Ca(OH)_2$ (slaked lime).

The alcoholic distillate produced from the treatment of the nejayote and the residues of an alkaline cooking can be considered with a sensory profile that is different from that obtained from any other process, which can be used for any use.

EXAMPLES

Example 1

An applied example of the invention made with cacahuazintle corn grains is cited below:

The process begins by placing the corn in a cooking pot with a total of 1000 L of water for 500 Kg of raw material, then slaked lime $(Ca(OH)_2)$ is added in a proportion of 1.15 Kg/100 Kg of raw material, cooking the corn grains approximately 30 to 90 minutes (time that can vary according to the characteristics and limitations of the equipment used and even the altitude at which the processing plant is located); once the cooking time is over, this preparation is left to rest around 12 h, a sensory evaluation of the cooked grain must be carried out and if approved, the process continues, which corresponds to washing the mixture.

The cooked grain is placed in a washing machine with clean water, where any remaining alkaline compound is removed. Once the washing process is finished, the cooked corn grain is collected in a draining vat, where the remaining water is drained for approximately 3 hours and a sensory evaluation of the cooked and washed grain (appearance, smell, consistency and taste) is carried out.

Subsequently, if the grain meets the sensory and quality standards, it is placed in a pre-drying vat where hot air is used for around 15 min. Afterwards, the cooked product is weighed (300 Kg) and loaded into the drum of the roaster where, with the help of a millworm, it is placed in the roaster, where the roasting and cleaning of waste begins for approximately 1 h at a temperature in the range of 85 to 100° C. with a suction of 100%. A sensory evaluation (visual control) is carried out in accordance with the dehydrated-roasting parameters mentioned above, if it is considered optimal, it is placed in roasting with a temperature between 100 and 115° (corresponding to a second roasting cycle), it is evaluated sensorially and with said analysis it is decided if the dehydrated-toasted grain has finished; upon completion, it is placed on a cooling bed.

The roasted-dehydrated corn load is stored in sacks until it is used in the alcoholic beverage manufacturing process (grinding, hydrolysis, fermentation and double distillation).

With respect to the residues from the alkaline cooking process, known as nejayote, they are subjected to a hydrolysis process using hydrolytic enzymes, where pH adjustments are previously made in a range between 4.5 to 6.0 (according to data provided by the supplier, the ranges may vary depending on the enzyme or enzymes used) to optimize the functioning of the enzymes and thus obtain a high level of hydrolyzed compounds, cacahuazintle corn flour is added and the enzymes are allowed to act until they have hydrolyzed the nejayote. At the end of the hydrolysis, the must is fermented using yeasts capable of fermenting in high concentrations of ethanol, finally the dead must is distilled to obtain alcohol for human consumption and/or industrial use.

Example 2

Below are provided data from a sensory evaluation of 4 samples of commercial white whiskey against the product from the second distillation of the alcoholic beverage, hereinafter referred to as "Abasolo whiskey" (prior to the aging process), as well as 4 samples of aged whiskey against Abasolo whiskey.

In this same sense, the differences in certain sensory attributes of both the product of the second distillation and the aged product of Abasolo whiskey with respect to different market samples are quantified.

Abasolo whiskey is a different alcoholic beverage due to its process of nixtamalization and roasting of cacahuazintle corn, causing changes and highlighting certain sensory attributes that make it unique in the category of this spirit. Similarly, the product resulting from the second distillation of Abasolo whiskey, prior to aging, is different from other spirits that do not undergo a maturation or aging process in barrels.

To carry out this evaluation and by consensus, different sensory attributes present in Abasolo whiskey were defined, which will be evaluated in the market samples, both in white spirits and in spirits aged in bourbon barrels, both produced with corn.

Methodology 10 sensory attributes were defined (Table 1).

TABLE 1

| Defined attributes |
| --- |
| Attributes |
| Corn |
| Nixtamalized Corn |
| Toasted corn |
| Caramel |
| Vanilla |
| Wood |
| Spiced |
| Sweet |
| Bitter |
| Body |

A sensory evaluation was carried out by a qualified panel, in which a 10-point hedonic scale was used to rate the intensity of each of the attributes (Table 2).

TABLE 2

| Hedonic scale used | |
| --- | --- |
| SCORE | EQUIVALENT |
| 0 | I pereceive it |
| 1 | It is perceived very light |
| 2 | It is slightly perceived |

TABLE 2-continued

| Hedonic scale used | |
| --- | --- |
| SCORE | EQUIVALENT |
| 3 | I perceive it as light to moderate |
| 4 | I perceive it moderately |
| 5 | I perceive it as moderate to considerable |
| 6 | I perceive it considerably |
| 7 | I perceive it slightly intense |
| 8 | I perceive it moderately intense |
| 9 | I perceive it very intense |

4 samples of white commercial spirits (Table 3) were selected for comparison with the spirit from the second distillation of Abasolo whiskey (prior to aging).

4 samples of commercial aged whiskey were selected (Table 3) to evaluate vs Abasolo whiskey.

TABLE 3

| Samples used to compare against the second distillation of Abasolo and Abasolo whiskey | |
| --- | --- |
| White whiskey samples (corn) | Aged whiskey samples (bourbon) |
| Midnight moonshine | Wild Turkey |
| Hookers house | Maker's Mark |
| Palmetto Moonshine | Jim Beam |
| Hudson NY | Bulleit |

By means of a spider graph and histogram, the perceptions of each of the attributes obtained in the study are shown.

A statistical analysis of variance (ANOVA) was performed to treat the data, using a reliability level of 95% and significance of 5%.

Results and Analysis

Second Distillation Spirits (Whites)

Statistical data were obtained for all the evaluations, with a total of 6 judges with a triplicate repetition to obtain a reliable statistical population, with a total of 18 analyzes per second distillation spirit sample. Table 4 lists the averages of the replicas corresponding to each attribute evaluated with respect to each sample analyzed.

TABLE 4

Average of data obtained by attribute corresponding to each evaluated sample (second distillation spirit)

| Spirit rectified | Corn | Nixt. Corn | Toast. Corn | Caramel | Vanilla | Wood | Spiced | Sweet | Bitter | Body |
| --- | --- | --- | --- | --- | --- | --- | --- | --- | --- | --- |
| Abasolo | 5.6 | 7.1 | 6.9 | 4.4 | 3.4 | 1.9 | 4.2 | 5.2 | 3.9 | 4.3 |
| Midnight | 0.2 | 0.0 | 0.1 | 2.4 | 1.6 | 0.9 | 2.8 | 3.9 | 4.0 | 3.4 |
| Hookers | 0.7 | 0.3 | 0.1 | 3.5 | 3.3 | 1.2 | 4.6 | 4.2 | 5.1 | 3.8 |
| Palmetto | 0.8 | 0.4 | 0.4 | 4.2 | 3.5 | 2.2 | 4.6 | 4.9 | 5.5 | 4.6 |
| Hudson | 1.2 | 0.0 | 0.1 | 3.7 | 3.0 | 1.9 | 4.4 | 4.2 | 5.0 | 4.2 |
| Average | 1.7 | 1.6 | 1.5 | 3.6 | 3.0 | 1.6 | 4.1 | 4.5 | 4.7 | 4.1 |

Figure 5:
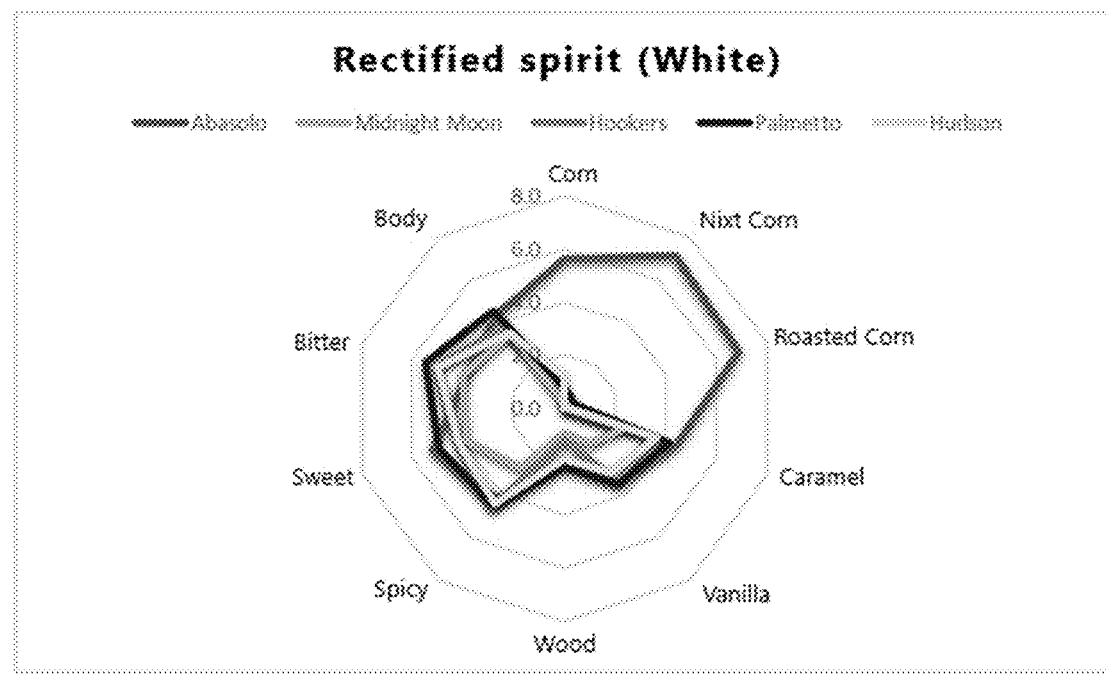
FIG. 5 shows a spider graph with the different attributes evaluated of distilled corn beverages ("white whiskey") with respect to samples of rectified spirits (whites), that is, with the result of the second distillation of the product carried out based on the present application.
Figure 6:
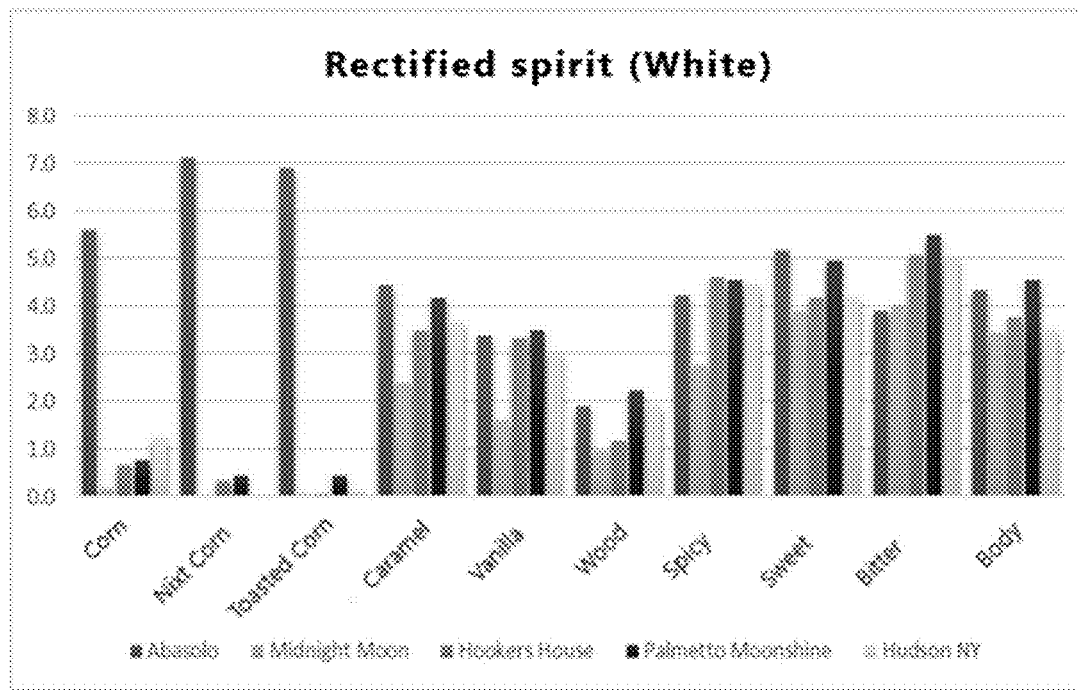
FIG. 6 shows a histogram of the attributes evaluated in the samples of white "whiskey" corn distillates with respect to the samples of rectified spirits (whites), second distillation of the present application.

FIG. 5 shows that the rectified spirit (Abasolo) presents greater intensity in the attributes of corn, nixtamalized corn and roasted corn; on the other hand, the intensity of the rest of the attributes is very close between the samples. FIG. 6 confirms what was previously mentioned.

Finally, for second distillation spirits (whites), we see in Table 5 the information corresponding to the ANOVA performed.

For the data obtained, it is observed in Table 5 that F> Critical value of F, therefore, there is a difference between the samples.

TABLE 5

ANOVA for White Whiskey

VARIANCE ANALYSIS

| Origin of variations | Sum of squares | Degs. of freedom | Average of squares | F | Probability | Critical value for F |
|---|---|---|---|---|---|---|
| Among groups | 78.12469136 | 9 | 8.680521262 | 3.246028448 | 0.004759043 | 2.124029264 |
| Within groups | 106.9679012 | 40 | 2.674197531 | | | |
| Total | 185.0925926 | 49 | | | | |

Aged Whiskey

For the samples of aged whiskey, the analyzes were carried out with a total of 6 judges and repetition in triplicate to obtain a reliable statistical population, with a total of 18 analyzes per sample of aged whiskey. Table 6 lists the averages of the replicas corresponding to each attribute evaluated with respect to each sample of aged whiskey analyzed.

TABLE 6

Average of data obtained by attribute corresponding to each evaluated sample (aged whiskey)

| | Corn | Nixt. Corn | Toast. Corn | Caramel | Vanilla | Wood | Spiced | Sweet | Bitter | Body |
|---|---|---|---|---|---|---|---|---|---|---|
| Abasolo | 6.1 | 7.3 | 7.4 | 5.1 | 4.5 | 5.3 | 4.4 | 5.7 | 3.8 | 4.9 |
| Wild Turkey | 0.6 | 0.0 | 0.0 | 5.4 | 5.6 | 6.6 | 5.1 | 5.7 | 4.4 | 4.8 |
| Maker's Mark | 0.4 | 0.0 | 0.3 | 4.9 | 5.2 | 6.3 | 5.6 | 5.3 | 5.4 | 5.1 |
| Jim Beam | 0.8 | 0.1 | 0.0 | 4.9 | 4.6 | 5.7 | 5.1 | 5.6 | 4.3 | 4.3 |
| Bulleit | 0.4 | 0.0 | 0.0 | 5.3 | 4.6 | 6.4 | 5.6 | 5.1 | 5.1 | 4.7 |
| Promedio | 1.7 | 1.5 | 1.5 | 5.1 | 4.9 | 6.1 | 5.1 | 5.5 | 4.6 | 4.8 |

Figure 7:
FIG. 7 shows a spider graph, where the different sensory attributes evaluated in commercial whiskey samples are presented with respect to the aged whiskey samples, prepared based on the present application.
Figure 8:
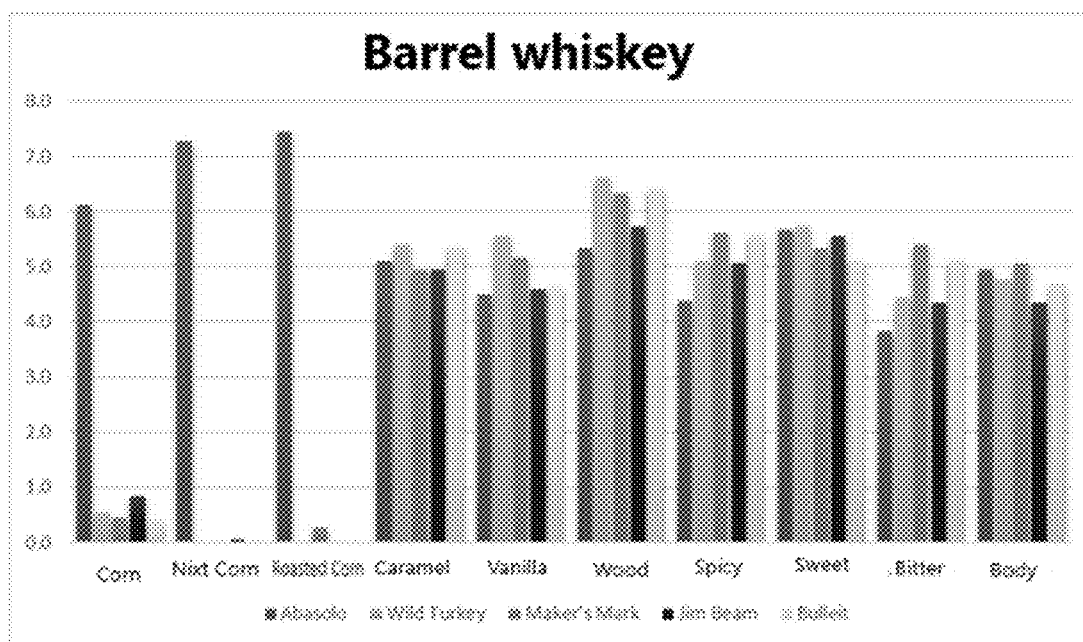
FIG. 8 shows a histogram of the attributes evaluated in the samples of commercial whiskey with respect to the samples of aged whiskey, prepared from the procedure described in the present application.

FIG. 7 shows that the Abasolo whiskey has a greater intensity in the attributes of corn, nixtamalized corn and toasted corn. On the other hand, for the rest of the attributes aged Abasolo is slightly less intense in terms of wood, spices, vanilla and caramel compared to the rest of the samples. FIG. 8 confirms what was previously mentioned.

Finally, for aged whiskey, we observe in Table 7 the information corresponding to the ANOVA of the samples studied.

For the data obtained, it is observed in Table 7 that F> Critical value of F, therefore, there is a difference between the samples.

TABLE 7

ANOVA for Aged Whiskey

VARIANCE ANALYSIS

| Origin of variations | Sum of squares | Degs. of freedom | Average of squares | F | Probability | Critical value for F |
|---|---|---|---|---|---|---|
| Among groups | 143.454949 | 9 | 15.93943377 | 5.504112152 | 6.45282E-05 | 2.124029264 |
| Within groups | 115.8365842 | 40 | 2.895914505 | | | |
| Total | 259.2915332 | 49 | | | | |

CONCLUSIONS

The spirit drink of second distillation of Abasolo (white), has a clear difference with respect to the rest of the samples studied in the attributes of corn, nixtamalized corn and toasted corn (FIGS. 5 and 6), while in the rest of the attributes they have similar intensities.

The Abasolo whiskey has a clear difference with respect to the rest of the samples studied in the attributes of corn, nixtamalized corn and roasted corn (FIGS. 7 and 8), it also differs for the rest of the attributes, being less for wood, spices, bitter and with less body.

In this regard, taking as a premise that the hypothesis Ho corresponds to that the samples are equal and Ha that the samples are different, according to the ANOVA analysis, it is observed that, if F<Critical value of F, the Ho is accepted (there is no difference between the samples) while if F> Critical value of F, then Ho is rejected (there is a difference between the samples). Therefore, with a degree of reliability of 95% and 5% significance, it is concluded that the spirit drink of second distillation is different from the rest of the samples analyzed, as well as Abasolo whiskey is different from the rest of the Aged whiskeys evaluated.

The present invention has been described in its preferred embodiments; however, it will be apparent to those skilled in the art that a multitude of changes and modifications may be made to this invention without departing from the scope of the following claims.

The invention claimed is:

1. A method of producing alcohol for human consumption and/or industrial use from the recovery and treatment of nejayote obtained from a nixtamalization process or alkaline cooking, comprising: —bringing water to the boiling point; —adding a compound that raises the pH in a range from 11 to 12.50 to a cooking pot to generate an alkaline solution; —placing corn or other grain in a cooking pot; —cooking the corn for approximately 30 minutes; —letting the corn rest for approximately 12 hours; —rinsing the corn or grain with clean water for a total of approximately 3 hours, trying to remove as much as possible the remains of the alkaline solution, nejayote; —adding a chemical compound to the nejayote in order to adjust the pH to about 6; —adding nixtamalized corn flour to the adjusted nejayote; —hydrolyzing the adjusted nejayote with hydrolytic enzymes until obtaining a must, wherein the hydrolytic enzymes are favorable for the liquefaction of starch and the hydrolysis of alpha-D-(1,4) glycosidic bonds, respectively; —fermenting the must with a yeast capable of withstanding an environment with an alcohol content; and—distilling the must.

2. The method according to claim 1, wherein the chemical compound to lower the pH is an inorganic acid.

3. The method according to claim 2, wherein the inorganic acid comprises hydrochloric acid.

* * * * *